(12) United States Patent
Osa

(10) Patent No.: US 8,179,657 B2
(45) Date of Patent: May 15, 2012

(54) EMISSION ANALYZER

(75) Inventor: Haruki Osa, Koka (JP)

(73) Assignee: Shimadzu Corporation, Kyoto (JP)

( * ) Notice: Subject to any disclaimer, the term of this patent is extended or adjusted under 35 U.S.C. 154(b) by 369 days.

(21) Appl. No.: 12/516,750

(22) PCT Filed: Dec. 13, 2006

(86) PCT No.: PCT/JP2006/324834
§ 371 (c)(1),
(2), (4) Date: May 28, 2009

(87) PCT Pub. No.: WO2008/072318
PCT Pub. Date: Jun. 19, 2008

(65) Prior Publication Data
US 2010/0073844 A1    Mar. 25, 2010

(51) Int. Cl.
*F23Q 3/00* (2006.01)
(52) U.S. Cl. ......................... 361/263; 361/247
(58) Field of Classification Search .................. 361/263, 361/247, 253
See application file for complete search history.

(56) References Cited

U.S. PATENT DOCUMENTS

| | | | | |
|---|---|---|---|---|
| 2004/0183507 | A1* | 9/2004 | Amei | 323/222 |
| 2004/0252990 | A1* | 12/2004 | Ichimasa | 396/206 |

FOREIGN PATENT DOCUMENTS

| | | |
|---|---|---|
| JP | 60-114746 A | 6/1985 |
| JP | 8-184564 A | 7/1996 |
| JP | 2000-9645 A | 1/2000 |
| JP | 2003-052173 A | 2/2003 |
| JP | 2004-144766 A | 5/2004 |
| JP | 2004-333323 A | 11/2004 |

OTHER PUBLICATIONS

Japanese Office Action dated Oct. 4, 2011, issued in corresponding Japanese Patent Application No. 2008-549153.

* cited by examiner

*Primary Examiner* — Danny Nguyen
(74) *Attorney, Agent, or Firm* — Sughrue Mion, PLLC

(57) ABSTRACT

After a switching element 13 is turned on, a charge controller 16 determines whether or not a current detected by an excitation current detector 15 has reached a predetermined level, and turns off the switching element 13 if the predetermined level has been reached. When the excitation current is controlled to a constant level, the excitation energy stored in a flyback transformer 12 also becomes constant, and this constant energy is stored in a capacitor 22 every time the switching element 13 is turned off. The charge control section 16 repeats the on/off operation of the switching element 13 a predetermined number of times at predetermined intervals of time before discontinuing the charging operation. Consequently, a constant amount of energy is held in the capacitor 22 when the charging operation is discontinued, and the period of time from the beginning to the completion of charging also becomes constant. Thus, the same conditions are constantly created while the spark discharge is repeated, so that the accuracy and reproducibility of the analysis are enhanced.

4 Claims, 2 Drawing Sheets

EMISSION ANALYZER

TECHNICAL FIELD

The present invention relates to an optical emission analyzer utilizing a spark discharge.

BACKGROUND ART

In a spark discharge emission analyzer, an amount of energy stored in a capacitor is supplied to a discharge electrode to generate a spark discharge between the electrode and a metallic sample, whereby the atoms of the elements contained in the metallic sample are vaporized, and the vaporized atoms are excited by a discharge plasma. Since each atom excited in the plasma emits light at a wavelength characteristic of the element, it is possible to determine the quantity of the element by dispersing the emitted light into a spectrum and measuring the light intensity at the aforementioned wavelength. It is also possible to perform a qualitative analysis of an unknown element contained in the sample by creating an emission spectrum with a predetermined wavelength range and searching for a wavelength at which a line spectrum is present. Normally, the spark discharge is repeated at a frequency from a few tens to several hundreds of hertz, and the photometrical values obtained for each discharge are integrated to improve the measurement accuracy.

In this type of emission analyzer, it is necessary to charge the capacitor to a voltage level of several hundreds of volts within a relatively short period of time to generate a spark discharge. For this purpose, a switching type capacitor-discharging circuit has been widely used in recent years (for example, refer to Patent Document 1). FIG. 3 is a block diagram showing the configuration of an emission analyzer using a conventional switching type capacitor-charging circuit.

In this emission analyzer, the emitting section consists of a capacitor-charging circuit 1, a capacitor circuit 2, an igniter circuit 3, and an emission stand 4. The capacitor-charging circuit 1 includes a direct-current (DC) power source 11, a flyback transformer 12 with primary and secondary windings, a switching element 13 such as a field-effect transistor (FET), and a charge controller 14 for driving the switching element 13. The capacitor circuit includes a rectifying diode 21, a discharge capacitor 22 for storing electrical energy to be used for generating a discharge, and a charged voltage detector 23 for detecting the charged voltage of the discharge capacitor 22. The igniter circuit 3 includes an igniter transformer 31 with primary and secondary windings, and an igniter driver 32 for generating a high level of voltage in the secondary winding of the igniter transformer 31. The emission stand 4 includes a discharge electrode 41 and a sample 42 to be measured, which is typically a piece of metal.

In the capacitor-charging circuit 1, the primary winding of the flyback transformer 12 and the switching element 13 are serially connected to both ends of the DC power source 11, respectively. When the switching element 13 is turned on (i.e. made to be conductive) by the charge controller 14, a DC current is supplied to the primary winding of the flyback transformer 12, whereby an excitation energy is stored in the flyback transformer 12. The charge controller 14 maintains the switching element 13 in the "on" state for a predetermined period of time. Subsequently, when the switching element 13 is turned off, a counter electromotive force arises in the secondary winding of the flyback transformer 12. As a result, the excitation energy that has been accumulated in the flyback transformer 12 is supplied through the rectifying diode 21 into the discharge capacitor 22 in the capacitor circuit 2. Thus, the discharge capacitor 22 is charged.

The on/off state of the switching element 13 is controlled as shown in FIG. 4. Every time the switching element 13 is turned off, the charged voltage of the discharge capacitor 22 increases in a stepwise manner due to the excitation energy that has been accumulated in the flyback transformer 12. The charged voltage detector 23 monitors the charged voltage of the discharge capacitor 22. Based on this monitored value, the charge controller 14 determines whether or not the charged voltage has exceeded a predetermined level V1. The charge controller 14 repeats the on/off controlling of the switching element 13 until the charged voltage exceeds the predetermined level V1. When the charged voltage has exceeded the predetermined voltage V1, the charge controller 14 stops turning on the switching element 13 to discontinue the charging of the discharge capacitor 22.

After the charging operation is completed in this manner, the igniter driver 32 in the igniter circuit 3 generates a high voltage in the igniter transformer 31, whereupon a spark discharge occurs between the discharge electrode 41 and the metallic sample 42. This makes the surface of the metallic sample 42 locally heated, vaporizing the atoms of an element present on the sample surface. Simultaneously, the energy stored in the discharge capacitor 22 is transferred into the gap between the discharge electrode 41 and the metallic sample 42 to create a plasma, in which the vaporized atoms are excited by electrons. When an atom returns from the excited state to a stable state, it emits light having a wavelength corresponding to the energy difference between the two states. The photometric section 5, which includes a light-dispersing element, photodetector and other components, measures the emitted light having a wavelength characteristic of the element to collect information relating to the elements contained in the metallic sample 42.

As just described, the capacitor-charging circuit 1 based on the conventional switching method accumulates a required amount of electrical energy in the discharge capacitor 22 by discontinuing the charging operation when the charged voltage of the discharge capacitor 22 has been found to be higher than the predetermined level V1.

However, the previously described capacitor-charging circuit 1 has the following problem: Since the period of time during which the switching element 13 is in the "on" state is definitely set, the amount of excitation energy that is accumulated within each on/off cycle of the switching element 13 changes if the voltage of the DC power source 11 changes. Furthermore, the capacitance of the discharge capacitor 22 varies due to, for example, a temperature change of the capacitor. Such a change in the amount of excitation energy accumulated in the flyback transformer 12 or the capacitance of the discharge capacitor 22 leads to a change in the number of on/off operations of the switching element 13 necessary for charging the discharge capacitor 22 to the constant voltage V1. Then, as shown in FIG. 5, the point in time at which the charged voltage of the discharge capacitor 22 exceeds the threshold level V1 will vary, which means that the charged voltage of the discharge capacitor 22 at the moment of discontinuing the charging operation can change by up to an amount corresponding to one on/off cycle of the switching element 13. Thus, the amount of energy to be accumulated in the discharge capacitor 22 changes.

Even if the charged voltage eventually reaches the same level, if the capacitance of the discharge capacitor 22 changes due to the aforementioned reason, the amount of energy held in the discharge capacitor 22 will change since the discontinuation of the charging operation is controlled based on the monitored value of the charged voltage of the same capacitor 22.

If the energy stored in the discharge capacitor 22 at the moment of generating the spark discharge is not constant, the state of the plasma at the moment of discharging will change. Therefore, even if the element content of the metallic sample 42 is the same, the emission intensity will vary, which may possibly deteriorate the accuracy or reproducibility of the analysis.

Patent Document 1: Japanese Unexamined Patent Application Publication No. 2004-333323 (Paragraphs 0004-0007; FIG. 5)

DISCLOSURE OF THE INVENTION

Problem to be Solved by the Invention

Thus, although it is essential for a spark discharge emission analyzer to constantly maintain the stored energy of the capacitor immediately before the discharging operation to enhance the accuracy and reproducibility of the analysis, it is difficult for the conventional system to maintain the stored energy at a constant level. The present invention has been developed to solve this problem, and its objective is to provide an emission analyzer in which the stability of the stored energy of the discharge capacitor for generating a spark discharge is improved to stabilize the emission of an objective element associated with the discharge.

Means for Solving the Problem

The present invention aimed at solving the previously described problem is an emission analyzer having a discharge electrode to be positioned leaving a predetermined gap to a sample, an igniter circuit connected to the discharge electrode, a capacitor for storing electrical energy to be used for discharging, and a capacitor-charging circuit for charging the capacitor, which is characterized by including:

a) a direct-current power source;
b) a flyback transformer with a primary winding connected to the direct-current power source and a secondary winding for supplying electrical energy to the capacitor;
c) a switching device for controlling the on/off state of an excitation current supplied from the direct-current power source to the primary winding of the flyback transformer;
d) a current detector for detecting the current value of the excitation current; and
e) a controller for controlling the operation of the switching device to repeat an on/off operation a predetermined number of times at predetermined intervals of time, the on/off operation including the steps of turning on the switching device and then turning off the switching device when the current value detected by the current detector has reached a predetermined value.

In the emission analyzer according to the present invention, the controller turns on the switching device to supply an excitation current to the primary winding of the flyback transformer, and then turns off the switching device to suspend the current supply when the excitation current has reached a predetermined fixed value. The excitation energy that will be accumulated in the flyback transformer depends on the inductance of the winding and the value of the current flowing through the winding. Therefore, by discontinuing the current supply when the current value has reached the predetermined value, it is possible to have the same amount of excitation energy accumulated in the flyback transformer within each on/off cycle of the switching device, regardless of the voltage of the direct-current power source. The controller charges the capacitor (i.e. transfers the excitation energy, which has been accumulated in the flyback transformer, to the capacitor) by repeating the on/off operation of the switching device a predetermined number of times. Therefore, the amount of energy held in the capacitor at the moment of discontinuing the charging operation will be constant.

The period of time from the beginning to the completion of charging is constant since both the number of repetitions of the on/off operation of the switching element and the interval of time (i.e. the time required for one on/off cycle of the switching element) are definitely set. If the period of time from the completion of charging to the initiation of the operation of the igniter circuit is constant, then the period of time from the beginning of charging to the initiation of the operation of the igniter circuit becomes constant, and the consumption (or loss) of energy due to, for example, the circuit for detecting the charged voltage of the capacitor also becomes constant. Therefore, the amount of energy stored in the capacitor immediately before the generation of spark discharge by the igniter circuit will be constant.

The amount of energy stored in the capacitor at the moment of discharging depends on the number of repetitions of the on/off operation of the switching device. Therefore, it is preferable that the number of repetitions can be externally set. It is also preferable that the predetermined value to be used as a reference for the current value of the excitation current to turn off the switching element can be externally set.

Effect of the Invention

In the emission analyzer according to the present invention, the amount of energy stored in the discharge capacitor at the moment of generating a spark discharge becomes constant without being affected by a voltage change of the DC power source, a capacitance change of the capacitor or other factors. As a result, the generation of plasma by the discharge will be performed in a stable manner and under virtually the same conditions, and the emission of an objective element within the plasma will also be stabilized. Thus, the emission analysis can be performed with higher levels of accuracy and reproducibility.

EXPLANATION OF NUMERALS

1 Capacitor-Charging Circuit
11 DC Power Source
12 Flyback Transformer
13 Switching Element
15 Excitation Current Detector
16 Charge Controller
2 Capacitor Circuit
21 Rectifying Diode
22 Discharge Capacitor
23 Charged Voltage Detector 3 Igniter Circuit
31 Igniter Transformer
32 Igniter Driver
4 Emission Stand
41 Discharge Electrode
42 Metallic Sample
5 Photometric Section

BEST MODE FOR CARRYING OUT THE INVENTION

Figure 1:
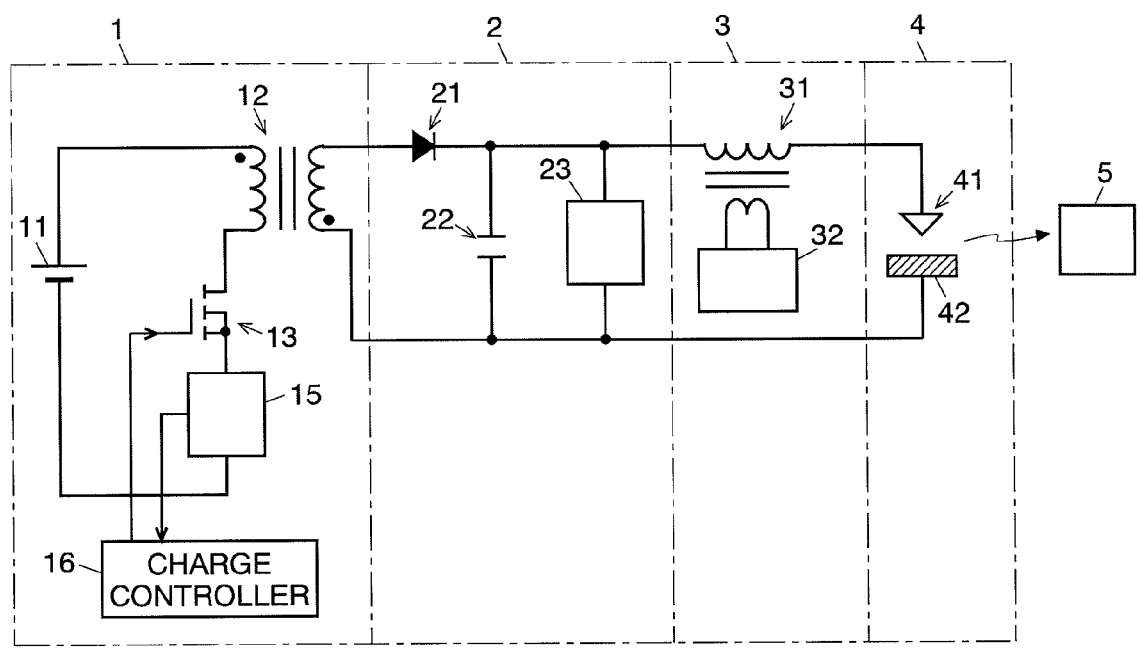
FIG. 1 is a block diagram mainly showing the emitting section of an emission analyzer according to an embodiment of the present invention.
Figure 2:
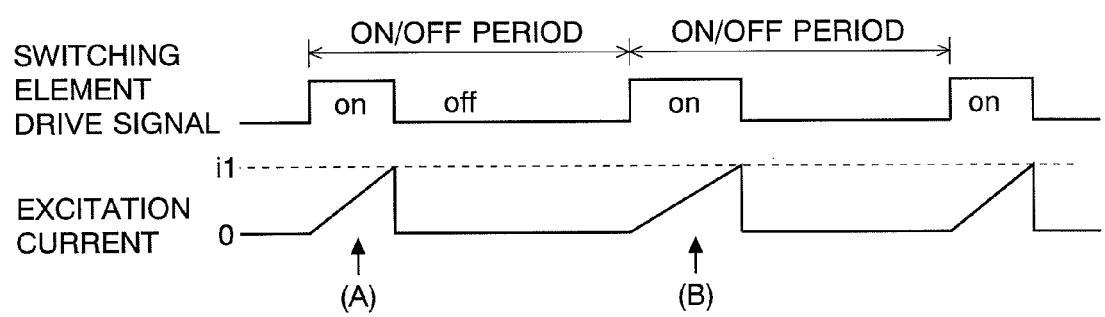
FIG. 2 is a principal timing chart in the emitting section of the emission analyzer according to the embodiment.
Figure 3:
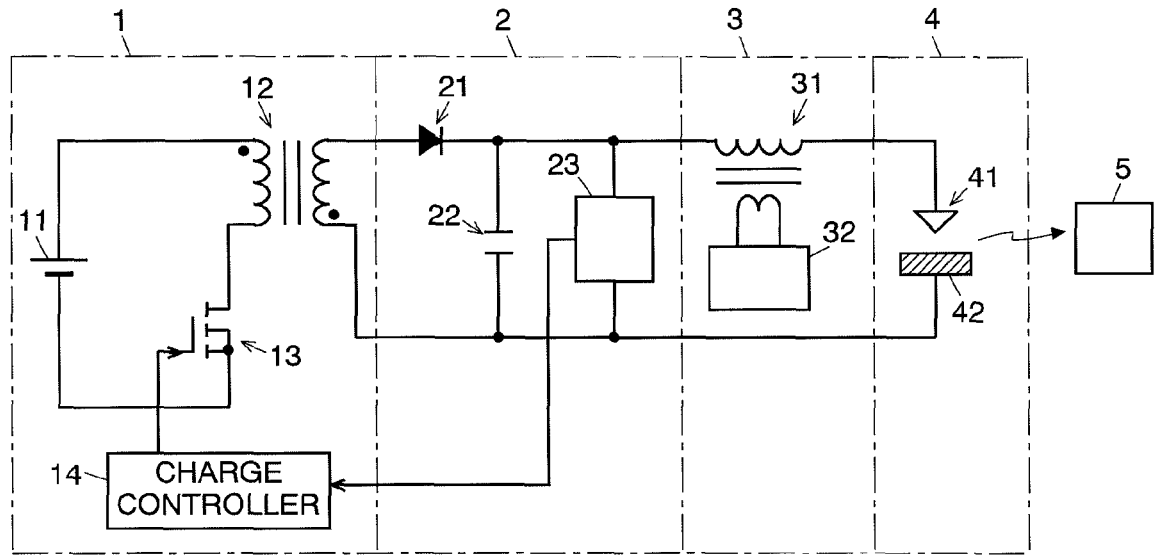
FIG. 3 is a block diagram showing the emitting section of a conventional emission analyzer.
Figure 4:
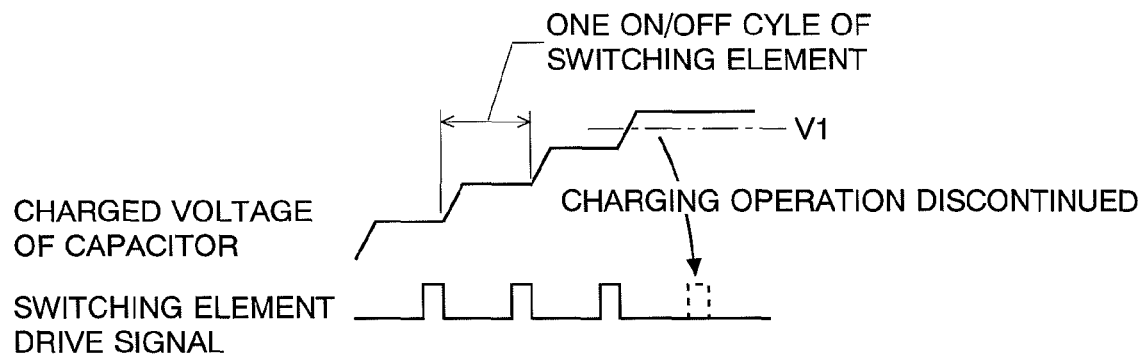
FIG. 4 is a waveform diagram in the main components of the emitting section of the conventional emission analyzer.
Figure 5:
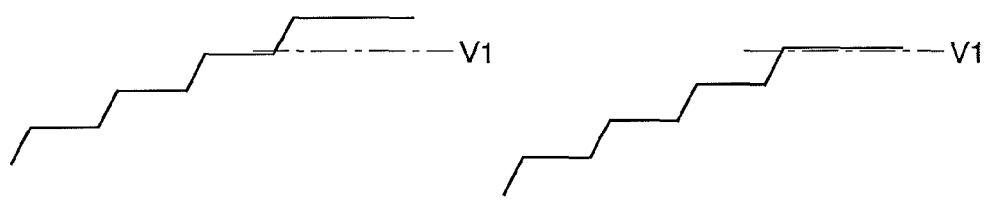
FIG. 5 is an illustration showing a variance of the charged voltage in the emitting section of the conventional emission analyzer.

One embodiment of the emission analyzer according to the present invention is hereinafter described with reference to the drawings. FIG. 1 is a block diagram mainly showing the emitting section of the emission analyzer according to the present embodiment, and FIG. 2 is its principal timing chart. The components identical to those of the conventional emission analyzer shown in FIG. 3 are denoted by the same numerals and hence will not be described in detail.

In the emitting section of the emission analyzer according to the present embodiment, the capacitor-charging circuit 1 has an excitation current detector 15 serially connected to the primary winding of the flyback transformer 12 and the switching element 13. The current value detected by the excitation current detector 15 is fed to the charge controller 16. The charge controller 16 determines the timing of the on/off operation of the switching element 13 with reference to the current detection value received from the excitation current detector 15 instead of the voltage value detected by the charged voltage detector 23. In the case of FIG. 1, the charged voltage detector 23 is employed for different purposes; for example, it is used to check whether or not the discharge capacitor 22 is correctly charged, prevent the capacitor from being overcharged, or detect the complete discharging of the capacitor.

In the emitting section, the following operations are consecutively performed: When the switching element 13 is turned on by the charge controller 16, a DC excitation current is supplied from the DC power source 11 to the primary winding of the flyback transformer 12, to accumulate excitation energy in the flyback transformer 12. As shown in FIG. 2, the excitation current almost linearly increases during the "on" period of the switching element 13. The value of this excitation current is continually detected by the excitation current detector 15, while the charge controller 16 determines whether or not the current value has reached a predetermined threshold level i1. If the excitation current has been determined to have reached the threshold level i1, the charge controller 16 immediately turns off the switching element 13, whereby the excitation current supply is discontinued. When the switching element 13 is turned off, a counter electromotive force arises in the secondary winding of the flyback transformer 12. Due to this force, the excitation energy that has been accumulated in the flyback transformer 12 is supplied into the discharge capacitor 22. Thus, the discharge capacitor 22 is charged.

In the charge controller 16, the length of time for one on/off cycle of the switching element 13 (i.e. the intervals of time from one turn-on action of the switching element 13 to the next) and the number of repetitions of the on/off operation are previously set. Accordingly, the charge controller 16 repeats the on/off operation of the switching element 13 the preset number of times at the preset intervals of time before discontinuing the charging operation.

A change in the voltage of the DC power source 11 changes the upward gradient of the excitation current during the "on" period of the switching element 13. For example, the upward gradient of the excitation current in phase (B) in FIG. 2 is smaller than that in phase (A) since the voltage of the DC power source 11 is lower in phase (B). Regardless of the gradient, the switching element 13 is maintained in the "on" state until the excitation current reaches the threshold level i1. Therefore, the "on" period of the switching element 13 does not always have the same length; a smaller upward gradient of the excitation current leads to a longer "on" period of the switching element 13. This increase in the length of the "on" period is accompanied by a corresponding decrease in the length of the "off" period since, as stated earlier, the length of time for one on/off cycle is definitely set (i.e. unchanged).

For an inductance L of the winding and excitation current I, the excitation energy E that will be accumulated in the flyback transformer 12 is indicated by:

$$E = (1/2) \cdot L \cdot I^2.$$

This equation states that the amount of excitation energy will be constant if the excitation current I is constant. Therefore, the same amount of excitation energy will be transferred from the flyback transformer 12 to the discharge capacitor 22 every time the switching element 13 is turned off. Since the number of on/off operations of the switching element 13 is definitely set, the discharge capacitor 22 will hold the same amount of stored energy when the charging operation is discontinued.

When, as described previously, the charging of the discharge capacitor 22 is completed, the igniter transformer 31 in the igniter circuit 3 under the command of a control circuit (not shown) generates a high voltage from the igniter driver 32 to produce a spark discharge between the discharge electrode 41 and the metallic sample 42 of the emission stand 4. The spark discharge vaporizes the atoms of the elements present on the surface of the metallic sample 42, and emissions of light originating from those elements occur within the plasma created between the discharge electrode 41 and the metallic sample 42.

Since the length of time for one on/off cycle of the switching element 13 and the number of repetitions thereof are constant, (these values are maintained at least throughout the analysis of one sample), the period of time from the beginning to the completion of charging is constant. Meanwhile, the electric charge held by the discharge capacitor 22 leaks to the charged voltage detector 23, which is connected to the discharge capacitor 22 in parallel, and a bleeder resistance (not shown), which is also connected to the discharge capacitor 22 in parallel for the sake of security. These elements consume a small portion of the stored electrical energy. However, the amount of this energy consumption also becomes constant since the aforementioned period of time is constant. Furthermore, since the length of time from the beginning of charging to the execution of discharging, i.e. to the initiation of the operation of the igniter circuit 3, is also constant, the discharge capacitor 22 will always hold the same amount of electrical energy when the discharging operation is performed.

In this manner, the same conditions can be constantly created for the spark discharge and emission within the plasma between the discharge electrode 41 and the metallic sample 42 in the case of periodically repeating the spark discharge. Thus, unfavorable variances of the photometrical values are suppressed to enhance the accuracy and reproducibility of the analysis.

From the preceding description, it is evident that changing the number of repetitions of the on/off operation of the switching element 13 will result in a different amount of energy stored in the discharge capacitor 22 when the discharging operation is performed. Accordingly, it is preferable to provide a means for changing the number of repetitions of the on/off operation if the discharge conditions should desirably be changed according to the sample type, a variance of the discharge atmosphere or other factors.

The previous embodiment is a mere example of the present invention; any modification, addition or correction that is appropriately made within the spirit of the present invention will evidently fall within the scope of the claims of this patent application.

The invention claimed is:

1. An emission analyzer having a discharge electrode to be positioned leaving a predetermined gap to a sample, an igniter circuit connected to the discharge electrode, a capacitor for storing electrical energy to be used for discharging, and a capacitor-charging circuit for charging the capacitor, which is characterized by comprising:
   a) a direct-current power source;
   b) a flyback transformer with a primary winding connected to the direct-current power source and a secondary winding for supplying electrical energy to the capacitor;
   c) a switching device for controlling an on/off state of an excitation current supplied from the direct-current power source to the primary winding of the flyback transformer;
   d) a current detector for detecting a current value of the excitation current; and
   e) a controller for controlling the operation of the switching device to repeat an on/off operation a predetermined number of times at predetermined intervals of time, the on/off operation including steps of turning on the switching device and then turning off the switching device when the current value detected by the current detector has reached a predetermined level, and for producing a spark discharge between the discharge electrode and the metallic sample of the emission stand after completing the on/off operation.

2. The emission analyzer according to claim 1, wherein a number of repetitions of the on/off operation of the switching device can be externally set.

3. The emission analyzer according to claim 1, wherein the predetermined value to be used as a reference for the current value of the excitation current to turn off the switching element can be externally set.

4. The emission analyzer according to claim 2, wherein the predetermined value to be used as a reference for the current value of the excitation current to turn off the switching element can be externally set.

\* \* \* \* \*